United States Patent [19]  [11] 3,984,411
Claverie et al.  [45] Oct. 5, 1976

[54] PYRIMIDINES
[75] Inventors: Jean-Marie Claverie; Georges Dominique Mattioda, both of Enghien-Les-Bains; Rene Jean Millischer, Pringy, all of France
[73] Assignee: Societe Generale de Recherches et d'Applications Scientifiques "Sogeras", Paris, France
[22] Filed: July 17, 1975
[21] Appl. No.: 596,880984411331003A424248

[52] U.S. Cl. .................... 260/247.5 D; 424/248; 260/251 R
[51] Int. Cl.² ..................... C07D 265/30
[58] Field of Search ............ 260/247.5 D

[56] References Cited
UNITED STATES PATENTS
3,259,623 7/1966 Kober et al. .......... 260/247.5 D
3,261,833 7/1966 Sutton et al. .......... 260/247.5 D
3,624,084 11/1971 Mathieu .............. 260/247.5 D Primary Examiner—Natalie Trousof
Assistant Examiner—Robert T. Bond
Attorney, Agent, or Firm—Beveridge, DeGrandi, Kline & Lunsford

[57] ABSTRACT
Compounds having the formula

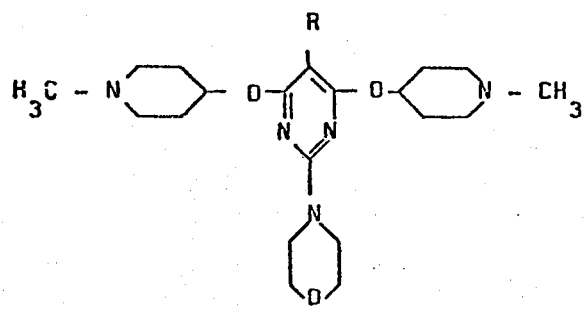

(I)

process for the preparation of such compounds which comprises reacting a compound having the formula:

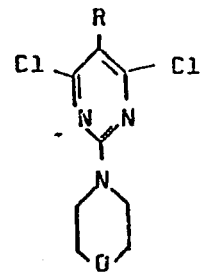

(II)

medicaments containing a compound of formula (I) or a salt thereof with a pharmaceutically acceptable acid; compounds of formula:

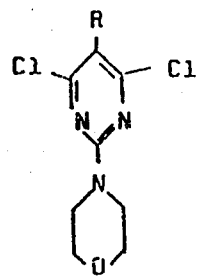

(II)

wherein R represents alkyl or alkoxy having 1 to 4 carbon atoms, benzyl, p-chlorophenyl or p-chlorophenoxy and compounds of formula:

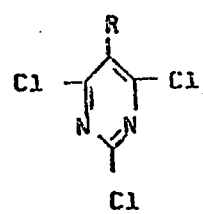

(III)

wherein R represents alkoxy having 2 to 4 carbon atoms, p-chlorophenyl or p-chlorophenoxy.

3 Claims, No Drawings

PYRIMIDINES

The present invention relates to new pyrimidines and to their use as medicaments for their hypoglycemiant and hypocholesterolemiant properties.

According to the present invention there are provided compounds having the formula:

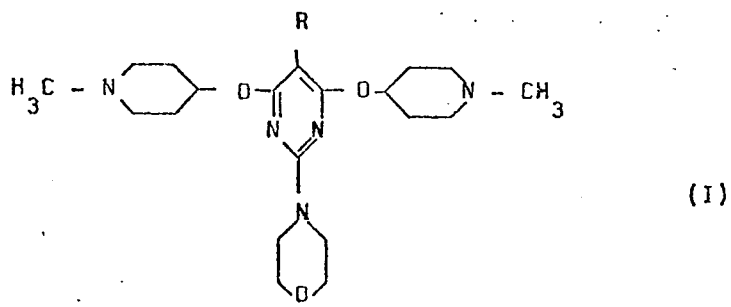

(I)

in which R represents a hydrogen or chlorine atom, an alkyl or alkoxy group containing 1 to 4 carbon atoms, a benzyl p-chlorophenyl or p-chlorophenoxy group.

The present invention also provides a process of preparing the compounds having formula (I) which comprises reacting a compound having the formula:

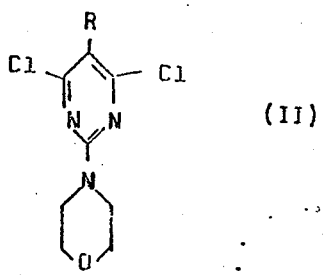

(II)

in which R has the same significance as in formula (I), with an excess of N-methyl-4-piperidinol in the presence of an alkaline agent such as, for example, caustic potash, at a temperature within the range 50°C to 160°C.

The compounds having formula (II), of which some are new products, may be prepared by reaction of the N-methyl morpholine with a compound having the formula:

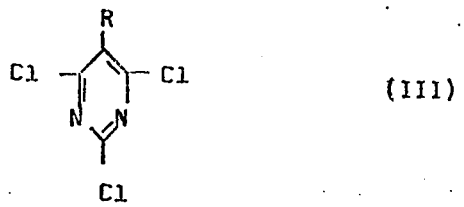

(III)

in which R has the same significance as in formula (I), according to the method described in the U.S. Pat. No. 3,259,623 granted on 5th July 1966.

The compounds having formula (II) may also be prepared by condensation of morpholino-4-carboxamidine with an ethyl malonate having the formula:

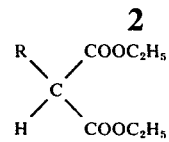

(IV)

in which R has the same significance as in formula (I), in the presence of an alkali metal alcoholate, to produce a 2-morpholino-4,6-dioxo-pyrimidine derivative, and reacting said 2-morpholino-4,6-dioxo-pyrimidine derivative obtained with a chlorinating agent such as, for example, phosphorus oxychloride The compounds having formula (III), some of which are new products, may be prepared by condensation, in the presence of an alkali metal alcoholate, of urea with an ethyl malonate of formula (IV) above and the action of a chlorinating agent such as phosphorus oxychloride on the 2,4,6-trioxo-pyrimidine derivative obtained.

The following Examples, in which the parts indicated are parts by weight unless the contrary is mentioned, illustrate the invention without restricting it thereto. The percentage analyses of the products described have given results of which the difference with respect to the calculated theoretical results remains within the absolute limits of error considered as suitable (±0.3%).

EXAMPLE 1

Preparation of
5-p-chlorophenoxy-2,4,6-trichloropyrimidine

A solution of sodium ethylate is prepared from 15.4 parts of sodium and 600 parts by volume of ethanol. 191.3 parts of ethyl p-chlorophenoxymalonate and 40 g of urea are added to this solution. The mixture is heated for 4 hours under reflux. The precipitate obtained is filtered off, then dissolved in 1000 parts of boiling water. The solution is acidified with 100 parts by volume of 10N hydrochloric acid. The precipitate which is formed is filtered off and dried. 140 parts of 5-p-chlorophenoxy-2,4,6-trioxo-pyrimidine which melts at a temperature above 260°C are thus obtained.

40 parts of 5-p-chlorophenoxy-2,4,6-trioxo-pyrimidine, prepared as indicated above, are introduced into a mixture of 100 parts by volume of phosphorus oxychloride and 45 parts by volume of dimethylaniline. The mixture is heated for 2 hours under reflux and then, after cooling, poured on a mixture of water and ice. The precipitate thus obtained is filtered off and dried. It is then melted and distilled under reduced pressure. 29 parts of 5-p-chlorophenoxy-2,4,6-trichloropyrimidine are thus obtained, in the form of a fraction passing over at 150°C under 0.2 mm Hg.

EXAMPLES 2 to 4

On operating as in Example 1, but replacing the ethyl p-chlorophenoxymalonate respectively by ethyl methoxymalonate, ethyl ethoxymalonate and ethyl p-chlorophenylmalonate, there are obtained:

5-methoxy-2,4,6-trichloro-pyrimidine (melting point 68°C)

5-ethoxy-2,4,6-trichloro-pyrimidine (melting point 54°C)

5-p-chlorophenyl-2,4,6-trichloro-pyrimidine (melting point 187°C)

EXAMPLE 5

Preparation of 2-morpholino-5-methoxy-4,6-dichloropyrimidine 150 parts by volume of benzene, 34 parts of 5-methoxy-2,4,6-trichloro-pyrimidine and 17.7 parts of N-methyl-morpholine are introduced into a reactor. The mixture is heated under reflux for 3 hours, then filtered and the solution is evaporated. The residue obtained is recrystallised from ethanol. 30 parts of 2-morpholino-5-methoxy-4,6-dichloro-pyrimidine of melting point 116°C are thus obtained.

EXAMPLES 6 to 12

By operating as in Example 5, but replacing the 5-methoxy-2,4,6-trichloro-pyrimidine by 5-methyl-2,4,6-trichloro-pyrimidine, 5-ethyl-2,4,6-trichloro-pyrimidine, 5-n-butyl-2,4,6-trichloro-pyrimidine, 5-p-chlorophenyl-2,4,6-trichloro-pyrimidine, 5-benzyl-2,4,6-trichloro-pyrimidine, 5-ethoxy-2,4,6-trichloro-pyrimidine and 5-p-chlorophenoxy-2,4,6-trichloro-pyrimidine, respectively there are obtained:

2-morpholino-5-methyl-4,6-dichloro-pyrimidine (melting point 86°C)

2-morpholino-5-ethyl-4,6-dichloro-pyrimidine (melting point 95°C)

2-morpholino-5-n-butyl-4,6-dichloro-pyrimidine (melting point 70°C)

2-morpholino-5-p-chlorophenyl-4,6-dichloro-pyrimidine (melting point 234°C)

2-morpholino-5-benzyl-4,6-dichloro-pyrimidine (melting point 90°C)

2-morpholino-5-ethoxy-4,6-dichloro-pyrimidine (melting point 99°C)

2-morpholino-5-p-chlorophenoxy-4,6-dichloro-pyrimidine (melting point 150°C).

EXAMPLE 13

Preparation of 2-morpholino-4,6-dichloro-pyrimidine

A solution of sodium ethylate is prepared from 72 parts of sodium and 1700 parts by volume of ethanol. 258 parts of 4-morpholinocarboxamidine chlorhydrate are added to this solution. The mixture is heated for 15 minutes under reflux, then the sodium chloride formed is separated by filtration. 249 parts of ethyl malonate are added to the filtrate and the mixture is maintained under reflux for 10 hours. The precipitate obtained is filtered off, then dissolved in water and the solution is acidified with 170 parts by volume of acetic acid. The precipitate which forms is filtered off, washed with water and dried. 184 parts of 2-morpholino-4,6-dioxo-pyrimidine which melts at a temperature above 300°C are thus obtained.

32 parts of 2-morpholino-4,6-dioxo-pyrimidine, prepared as indicated above, are dissolved in 150 parts by volume of phosphorus oxychloride. The solution is heated under reflux for 4 hours and then, after cooling, the reaction mixture is poured into a mixture of water and ice. The precipitate obtained is separated by filtration. 15 parts of 2-morpholino4,6-dichloro-pyrimidine which melts at 140°C are obtained by recrystallisation from ethanol.

EXAMPLE 14

Preparation of 2-morpholino-4,6-di[(N-methyl-4'-piperidyl)oxy]-5-methoxy-pyrimidine 54 parts of N-methyl-4-piperidinol and 14 parts of caustic potash pellets are introduced into a reactor. The mixture is heated to 60°C, then 26.4 parts of 2-morpholino-5-methoxy-4,6-dichloro-pyrimidine are introduced in small portions while the temperature is maintained at about 60°C. The mixture is then heated at 130°C for 3 hours. After cooling, an extraction is effected with an ether-water mixture. The organic phase is separated, washed until the washings are neutral, dried over anhydrous sodium sulphate and concentrated by evaporation. The solid residue obtained is recrystallised from ethyl acetate. 22 parts of 2-morpholino 4,6-di[(N-methyl-4'-piperidyl) oxy]-5-methoxy-pyrimidine of melting point 140°C are thus obtained.

EXAMPLES 15 to 23

The operator is as in Example 14, but the 2-morpholino-5 methoxy-4,6-dichloro-pyrimidine is replaced by other 2-morpholino-4,6-dichloro-pyrimidine derivatives of which the preparation has been described above. The molar proportions of N-methyl-4-piperidinol, caustic potash and 2-morpholino-4,6-dichloro-pyrimidine derivative are the same as in Example 14. The following compounds are thus obtained (the compounds are given either in the form of the free base, or in the form of a salt of the base with a pharmaceutically acceptable acid):

| Example | Compound obtained | Melting point |
|---|---|---|
| 15 | 2-moropholino-4,6-di[(N-methyl-4'-piperidyl)oxy]-5-methyl-pyrimidine | 124°C |
| 16 | 2-morpholino-4,6-di[(N-methyl-4'-piperidyl)oxy]-5-ethyl-pyrimidine dihydrobromide | 245°C |
| 17 | 2-morpholino-4,6-di[(N-methyl-4'-piperidyl)oxy]-5-n-butyl-pyrimidine dihydrochloride | 270°C |
| 18 | 2-morpholino-4,6-di[(N-methyl-4'-piperidyl)oxy]-5-p-chlorophenyl-pyrimidine | 169°C |
| 19 | 2-morpholino-4,6-di[(N-methyl-4'-piperidyl)oxy]-5-ethoxy-pyrimidine dihydrochloride | 275°C |
| 20 | 2-morpholino-4,6-di[(N-methyl-4'-piperidyl)oxy]-5-p-chlorophenoxy-pyrimidine | 152° |
| 21 | 2-morpholino-4,6-di[(N-methyl-4'-piperidyl)oxy]-5-benzyl-pyrimidine | 129°C |
| 22 | 2-morpholino-4,6-di[(N-methyl-4'-piperidyl)oxy]-5-chloro-pyrimidine | 153°C |
| 23 | 2-morpholino-4,6-di[(N-methyl-4'-piperidyl)oxy]-pyrimidine | 130°C |

TOXICOLOGICAL PROPERTIES

The toxicities of the compounds according to the invention have been determined on mice CD 1 (Charles RIVER) by intravenous and oral applications. The LD 50, calculated by the cumulative quantal method of J. J. Reed and H. Muench, Am. J. Hyg., 27, 493 (1938) are listed in the following Table:

| Product of Example | Intense toxicities to mice (LD 50 mg/kg) | |
|---|---|---|
| | intravenous | oral |
| 15 | 81 | atoxic at 900 |
| 16 | 54 | about 525 |
| 17 | — | about 225 |
| 18 | 20 | about 600 |
| 19 | 70 | about 600 |
| 20 | — | above 900 |
| 21 | 40 | about 800 |
| 22 | — | atoxic at 900 |
| 23 | — | atoxic at 900 |
| 14 | 67 | atoxic at 900 |

On the whole, the products according to the invention are not very toxic to mice since, taken orally, some are atoxic at 900 mg/kg and the others have LD 50 between 225 and more than 900 mg/kg, while, taken intravenously, the LD 50 are between 20 and 81 mg/kg.

PHARMACOLOGICAL PROPERTIES

1. Hypocholesterolemiant properties

The hypocholesterolemiant effects of the products according to the invention have been studied on the rat CD (Charles RIVER) by oral application. The animals, divided into groups of 10, are treated daily by gastric probe for 4 consecutive days. Four hours after the last administration, the rats are killed and their blood is collected in order to proceed to the determination of the amount of cholesterol according to the method of J. Levine and B. Zak, Clin. Acta, 10, 381 (1964).

The activity of the substances is evaluated by calculating the percentage variation of the average amount of cholesterol of the animals treated with respect to that of the control animals. Then the statistical significance of the differences observed is determined by application of the STUDENT test.

The results obtained are listed in the following Table.

| Product of Example | Dose in mg/kg taken orally | Variation of the cholesterolemia in % with respect to the controls after 4 days treatment |
|---|---|---|
| 15 | 50 | −31+++ |
| 16 | 100 | −60+++ |
| 17 | 100 | −36+++ |
| 18 | 100 | −14+ |
| | 300 | −44+++ |
| 20 | 100 | −47+++ |
| 21 | 100 | −39+++ |
| 22 | 50 | −19+++ |
| | 100 | −45+++ |

Significance of the variations:
+significant difference for p = 0.05
+++significant difference for p = 0.001

The product of all these Examples exert remarkable hypocholesterolemiant activities, especially those of Examples 15, 16, 20 and 22.

2. Hypoglycemiant properties

The hypoglycemiant properties have been studied on the male rat CD (Charles RIVER) of 200–250 g, of which the glycemia is controlled after 4 days of daily treatment by oral application. The serum glucose is determined by the method of W. S. Hoffman, J. Biol. Chem., 120, 51 (1937). Groups of 10 rats are used and the hypoglycemiant activity is expressed by the percentage variation of the average glycemia of the treated animals compared with that of the controls. The statistical significance of the differences observed is determined by application of the STUDENT test.

The results are collected in the following Table:

| Product of Example | Dose in mg/kg taken orally | Percentage variation of the glycemia compared with the controls after 4 days treament |
|---|---|---|
| 15 | 50 | −12+ |
| 18 | 100 | −29+++ |
| | 300 | −35+++ |
| 19 | 300 | −43+++ |
| 20 | 300 | −27+++ |
| 21 | 100 | −27+++ |
| 23 | 400 | −20+++ |
| 14 | 200 | −24+++ |

Significance of the variations:
+significant difference for p = 0.05
+++significant difference for p = 0.001

The products of Examples 18, 19, 20 and 21 exert especially large hypoglycemiant effects.

THERAPEUTIC APPLICATION

The products according to the invention and their salts with pharmaceutically acceptable acids may be used in human therapeutics as hyprcholesterolemiants and as hypoglycemiants or antidiabetics. They may be administered in the form of compressed tablets, lozenges, gelatine-coated pills, cachets, suppositories, drops, etc. in unit doses of between 25 and 500 mg at a daily dosage going from 100 to 2500 mg, according to the forms and the compounds.

We claim:

1. A compound having the formula:

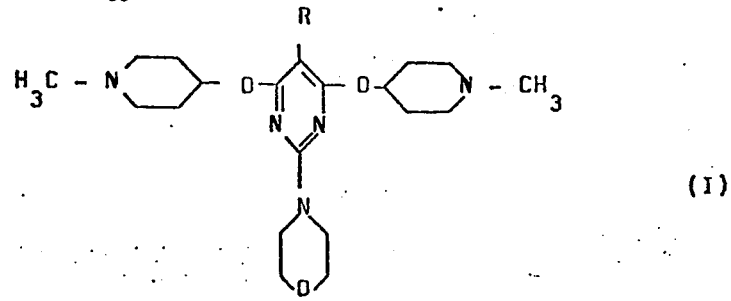

(I)

in which R represents a hydrogen or chlorine atom, $C_1$-$C_4$ alkyl, $C_1$-$C_4$ alkoxy, a benzyl p-chlorophenyl or p-chlorophenoxy group.

2. A process for the preparation of a compound having the formula:

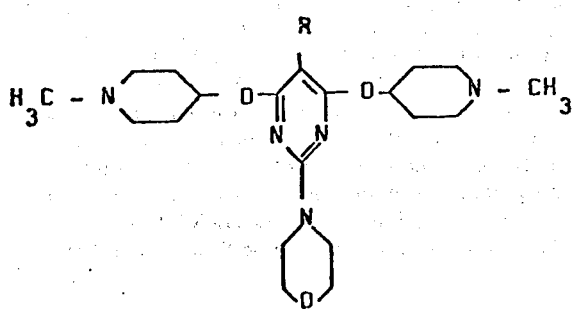

(I)

in which R represents a hydrogen or chlorine atom, $C_1$-$C_4$ alkyl, $C_1$-$C_4$ alkoxy, a benzyl p-chlorophenyl or p-chlorophenoxy group, which comprises reacting a compound having the formula:

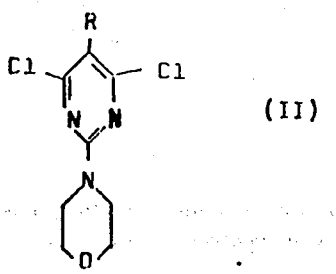

(II)

in which R has the same significance as in formula (I), with an excess of N-methyl-4-piperidinol in the presence of an alkaline agent, at a temperature in the range of 50° to 160°C.

3. A process according to claim 2 wherein the compound of formula (II) is prepared by condensation of morpholino-4-carboxamidine with an ethyl malonate of the formula:

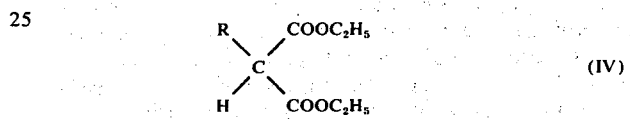

(IV)

in which R has the same significance as in formula (I), in the presence of an alkali metal alcoholate, to produce a 4,6-dioxo-2-morpholino-pyrimidine derivative, and reacting said 4, 6-dioxo-2-morpholino-pyrimidine derivative with a chlorinating agent.

* * * * *

UNITED STATES PATENT AND TRADEMARK OFFICE
CERTIFICATE OF CORRECTION

PATENT NO. : 3,984,411

DATED : Oct. 5, 1976

INVENTOR(S) : Jean-Marie Claverie; Georges Dominique Mattioda; Rene Jean Millischer It is certified that error appears in the above–identified patent and that said Letters Patent are hereby corrected as shown below:

The Application No. should read 596,880.

Signed and Sealed this

Eleventh Day of January 1977

[SEAL]

Attest:

RUTH C. MASON
Attesting Officer

C. MARSHALL DANN
Commissioner of Patents and Trademarks

UNITED STATES PATENT AND TRADEMARK OFFICE
CERTIFICATE OF CORRECTION

PATENT NO. : 3,984,411
DATED : October 5, 1976
INVENTOR(S) : Jean-Marie Claverie et al It is certified that error appears in the above-identified patent and that said Letters Patent are hereby corrected as shown below:

Under the provisions of 35 U.S.C. 119, applicants claim the benefit of the filing date of French application No. 75 11154, filed April 10, 1975.

Signed and Sealed this

Seventeenth Day of May 1977

[SEAL]

Attest:

RUTH C. MASON
*Attesting Officer*

C. MARSHALL DANN
*Commissioner of Patents and Trademarks*